(12) United States Patent
Gordon et al.

(10) Patent No.: US 9,359,319 B2
(45) Date of Patent: Jun. 7, 2016

(54) HYDROGENATION OF BIOMASS-DERIVED SUBSTRATES

(71) Applicant: Los Alamos National Security, LLC, Los Alamos, NM (US)

(72) Inventors: John C. Gordon, Los Alamos, NM (US); Christopher R. Waidmann, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 14/386,381

(22) PCT Filed: Mar. 13, 2013

(86) PCT No.: PCT/US2013/030710
§ 371 (c)(1),
(2) Date: Sep. 19, 2014

(87) PCT Pub. No.: WO2013/142177
PCT Pub. Date: Sep. 26, 2013

(65) Prior Publication Data
US 2015/0057457 A1    Feb. 26, 2015

Related U.S. Application Data

(60) Provisional application No. 61/614,414, filed on Mar. 22, 2012.

(51) Int. Cl.
| | |
|---|---|
| *C07D 307/02* | (2006.01) |
| *C07D 307/46* | (2006.01) |
| *B01J 31/02* | (2006.01) |
| *B01J 31/30* | (2006.01) |
| *B01J 31/24* | (2006.01) |
| *C07D 307/42* | (2006.01) |

(52) U.S. Cl.
CPC ............ *C07D 307/46* (2013.01); *B01J 31/0267* (2013.01); *B01J 31/2495* (2013.01); *B01J 31/30* (2013.01); *C07D 307/42* (2013.01); *B01J 2231/645* (2013.01); *B01J 2531/16* (2013.01); *B01J 2531/822* (2013.01)

(58) Field of Classification Search
CPC .... C07D 307/42; B01J 31/2495; B01J 31/30; B01J 31/0267; B01J 2531/16; B01J 2231/645; B01J 2531/822
USPC .................... 549/498, 497; 502/152
See application file for complete search history.

(56) References Cited

U.S. PATENT DOCUMENTS

| | | |
|---|---|---|
| 2003/0125563 A1 | 7/2003 | Buchwald et al. |
| 2008/0033171 A1 | 2/2008 | Buchwald et al. |
| 2009/0124839 A1* | 5/2009 | Dumesic et al. ............ 585/251 |
| 2009/0203927 A1 | 8/2009 | Shimizu et al. |

FOREIGN PATENT DOCUMENTS

WO    2008/151178    12/2008

OTHER PUBLICATIONS

Addis et al., "Selective Reduction of Carboxylic Acid Derivatices by Catalytic Hydrosilylation," Angew. Chem. Int. Ed., Jun. 2011, vol. 50, pp. 6004-6011.
Alonso et al., "Catalytic conversion of biomass to biofuels," Green Chem., Aug. 2010, vol. 12, pp. 1493-1513.
Baker et al "(BDH)CuH: A "Hot" Styrker's Reagent for Use in Achiral Conjugate Reductions," Org. Lett., 2008, vol. 10, pp. 289-292, first published online Dec. 2007.
Chen et al., "Highly Chemoselective Catalytic Hydrogenation of Unsaturated Ketones and Aldehydes to Unsaturated Alcohols Using Phosphine-Stabilized Copper(I) Hydride Complexes," Tetrahedron, Apr. 2000, vol. 56, pp. 2153-2166.
Chen et al., "Phosphine Effects in the Copper(I) Hydride-Catalyzed Hydrogenation of Ketones and Regioselective 1,2-Reduction of α,β-Unsaturated Ketones and Aldehydes, Hydrogenation of Decalin and Steroidal Ketones and Enones," Tetrahedron, Apr. 2000, vol. 56, pp. 2789-2798.
Deutsch et al., "CuH-Catalyzed Reactions," Chem. Rev., Jul. 2008, vol. 108, pp. 2916-2927.
Diaz-Torres et al. "Coordinating ability of anions and solvents towards transition metals and lanthanides," Dalton Trans., Sep. 2011, vol. 40, pp. 10742-10750.
Dierkes et al., "The bite angle makes the difference: a practical ligand parameter for diphosphine ligands," J. Chem. Soc. Dalton Trans., Jan. 1999, pp. 1519-1529.
Dong et al., "Theoretical investigation oncopper hydrides hydrosilylation reaction of 3-methylcyclohex-2-enone: mechanism and ligands' effect," Catal. Sci. Technol., 2012, vol. 2, pp. 564-569, piblished online Dec. 2011.
Du et al., "Mechanistic Insight into Hydrosilylation Reactions Catalyzed by High Valent Re=X(X=O, Nar, or N) Complexes: The silane (Si-H Does Not Add across the Metal-Ligand Multiple Bond," J. Am. Chem. Soc., Mar. 2007, vol. 129, pp. 5180-5187.
Gathy et al., "A theorectical study of the electric field effect of the ligand bite angle on the hydrosilylation reaction of ketones by Cu(I) diphosphine complexes," J. Organomet. Chem., Oct. 2011, vol. 696, pp. 3425-3430.
Gathy et al., Mechanism of ketone hydrosilylation by (Cu(I) catalysts: A theoretical study, J. Organometallic Chem., Aug. 2009, vol. 694, pp. 3943-3950.
Goeden et al., "A Cu-(μ—H) Bond Can Be Stronger Than an Intramolecular P→Cu Bond. Synthesis and Structure of Cu2(μ—H)2[η2—CH3C(CH2PPh2)3]2," Inorg. Chem., Jul. 1986, vol. 25, pp. 2484-2485.

(Continued)

*Primary Examiner* — T. Victor Oh
(74) *Attorney, Agent, or Firm* — Lewis Roca Rothgerber Christie LLP

(57) ABSTRACT

The α,β-unsaturated ketone moiety of a substrate representative of non-food based biomass was hydrogenated to the corresponding saturated alcohol moiety using a composition including (1) a copper salt; (2) a phosphine; (3) a polar aprotic solvent such as acetonitrile, and (4) a compound suitable for providing hydrogen for the hydrogenation, such as a suitable silane material or a suitable siloxane material.

6 Claims, No Drawings

(56) References Cited

OTHER PUBLICATIONS

Hughes et al., "Catalytic Enantioselective Conjugate Reduction of Lactones and Lactams," J. Am. Chem. Soc., Aug. 2003, vol 125, pp. 11253-11258.

Issenhuth et al.. "Mechanistic Studies on the Copper-Catalyzed Hydrolisylation of Ketones," Eur. J. Inorg. Chem., 2010, pp. 529-541, first published online Nov. 2009.

Khalimon et al., "Mechanistic Aspects of Hydrosilylation Catalyzed by (ArN=)Mo(H)(CI)PMe3)3," Inorg. Chem., Mar. 2012, vol. 51, pp. 4300-4313.

Li et al., "Conjugate reduction and reductive aidol cyclization of α,β-unsaturated thioesters catalyzed by (BDP)CuH," Org. Biomol. Chem., Jun. 2011, vol. 9, pp, 6143-6147.

Lipschutz et al, "Asymmetric Hydrosilylation of Aryl Ketones Catalyzed by Copper Hydride Complexed by Nonracemic Biphenyl Bisphosphine Ligands," J. Am. Chem. Soc., Jun. 2003, vol. 125, pp. 8779-8789.

Lipshutz et al., "Asymmetric 1,4-Reductions of Hindered β-Substituted Cycloalkenones Using Catalytic SEGPHOS-Ligated CuH," Org. Lett , Mar. 2004, vol. 6, pp. 1273-1275.

Lipshutz et al., "Tweaking Copper Hydride (CuH) for Synthetic Gain. A Practical, One-Pot Conversion of Dialkyl Ketones to Reduced Trialkysilyl Ether Derivatives," Org. Lett., Aug. 2003, vol. 5, pp. 3085-3088.

Mahoney et al., "Selective Hydride-Mediated Conjugated Reduction of α,β-Unsaturated Carbonyl Compounds Using [(Ph3P)CuH]6," J. Am. Chem. Soc., Jan. 1988, vol. 110, pp. 291-293.

Mankad et al., "Synthesis, Structure, and Alkyne Reactivity of a Dimeric (Carbene)copper(I) Hydride," Organometallics, Jun. 2004, pp. 3369-3371.

Mortenson et al., "A review of catalytic upgrading of bio-oil to engine fuels," Appl. Cat. A, Sep. 2011, vol. 407, pp. 1-19.

Moser et al., "CuH-Catalyzed Enantioselective 1,2-Reductions of α, β-Unsaturated ketones," J. Am. Chem. Soc., May 2010, vol. 132, pp. 7852-7853.

Mostefai et al., "Air-Accelerated Enantioselective Hydrosilylation of Ketones Catalyzed by Copper(I) Fluoride-Diphosphine Complexes: Investigations of the Effects of Temperature and Ligand Structure," Synthesis, Mar. 2007, pp. 1265-1271.

Nolin et al., "Analysis of an Unprecedented Mechanism for the Catalytic Hydrosilylation of Carbonyl Compounds," J. Am Chem Soc., Nov. 2007, vol. 129, pp. 14684-14696.

Sass et al., "Solvent Effect in Reactions Using Stryker's Reagent," J. Org. Chem., Sep. 2012 vol. 7, pp. 9374-9378.

Schlaf, "Selective deoxygenation of sugar polyols to α,ω-diols and other oxygen content reduced materials—a new challenge to homogeneous ionic hydrogenation and hydrogenolysis catalysis," Dalton Transactions, Aug. 2006; pp. 4645-4653.

Serrano-Ruiz et al., "Catalytic routes for the conversion of biomass into liquid hydrocarbon transportation fuels," Energy Environ. Sci, 2011, vol. 4, pp. 83-99, published online on Nov. 2010.

Shirobokov et al., "Nonhydride Mechanism of Metal-Catalyzed Hydrosilylation," J. Am. Chem. Soc., Apr. 2011, vol. 133, pp. 6487-6489.

Sirol et al., "Efficlent Enantioselectve Hydrosilylation of Ketones Catalyzed by Air Stable Copper Fluoride-Phosphine Complexes", Org. Lett., Nov. 2001, vol. 3, pp. 4111-4113.

Sue et al., "CuII-Catalyzed Asymmetric Hydrosilylation of Diaryl- and Aryl Heteroaryl Ketones: Application in the Enantioselective Synthesis of Orphenadrine and Neobenodine," Chem-Eur. J., May 2012, vol. 18, pp. 7486-7492.

Suresh et al., "Quatifying the Electronic Effect of Substituted Phosphine Ligands via Molecular Electrostatic Potential," Inorg. Chem., Feb. 2002, vol. 41, pp. 1573-1578.

Tolman, "Steric Effects of Phosphorus Ligands in Organometallic Chemistry and Homogeneous Catalysis," Chem. Rev., Jun. 1977, vol. 77, pp. 313-348.

Waidmann et al., "Functional group dependence of the acid catalyzed ring opening of biomass derived furan rings: an experimental and theoretical study," Catal. Sci. Tethnol., Jan. 2013, vol. 3, pp. 106-115.

Waidmann et al., "One-pot reduction of olefin and ketone moieties by a copper-phosphine catalyst enabled by polar aprotic solvents," Catalysis Science & Technology, published Feb. 2013.

Wu et al., "A remarkably effective copper(II)-dipyridylphosphine catalyst system for the asymmetric hydrosilylation of ketones in air,"0 PNAS, Feb. 2005, vol. 102, pp. 3570-3575.

Zhang et al., "Application of Copper(II)-Dipyridylphosphine Catalyst in the Asymmetric Hydrosilylation of Simple Ketones in Air," Chem.-Eur, J., May 2009, vol, 15, pp. 5888-5891.

International Search Report for PCT/US2013/030710 mailed May 15, 2013.

Written Opinion of the International Searching Authority for PCT/US20113/030710 mailed May 15, 2013.

* cited by examiner

HYDROGENATION OF BIOMASS-DERIVED SUBSTRATES

RELATED APPLICATIONS

This is the U.S. National Stage of International Application No. PCT/US2013/030710, filed Mar. 13, 2013, which claims the benefit of U.S. Provisional Application No. 61/614,414, entitled "Reduction of Olefin and Ketone Groups in Non-Food Biomass Derived Substrates Using Copper-Phosphine Catalysts," filed on Mar. 22, 2012. The provisional application is incorporated herein in its entirety.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to hydrogenation of non-food based biomass substrates.

BACKGROUND OF THE INVENTION

The field of homogeneous transition-metal catalysis has focused on the development of chemoselective, regioselective, and enantioselective catalysts and processes. Development of selective processes has been driven largely by the under-functionalized nature of petrochemical substrates. By contrast, for the efficient hydrogenation of non-food derived biomass substrates, less selective catalysts that can hydrogenate and perhaps deoxygenate a wide variety of functional groups in as few steps as possible are preferred. Preferred compositions effective for hydrogenating non-food biomass derived substrates should be tolerant of ketone and alcohol moieties present in these substrates. They should also be tolerant of water formed during the hydrogenation. They would preferably be inexpensive, and they would perform effectively at modest temperatures and pressures. These compositions would also preferably provide homogeneous catalysts because homogeneous catalysts offer a capability of rational tuning of the catalyst environment, which is not possible with heterogeneous precious metal catalysts.

Compositions derived from copper compounds and phosphines have been reported to provide homogeneous catalysts that mediate a variety of hydrogenations. They have also been reported to be tolerant to air, water, and alcohol moieties. However, the development of copper-phosphine catalysts has thus far focused on high chemoselectivity and high stereoselectivity, which are not aspects of a hydrogenation of non-food biomass derived substrates.

SUMMARY OF THE INVENTION

An embodiment composition comprises a homogeneous catalyst effective for hydrogenation of an α,β-unsaturated ketone moiety of a substrate comprising a furan ring. The composition is prepared by combining a copper salt, a phosphine, a polar aprotic solvent, and a material suitable for providing hydrogen for the hydrogenation, the suitable materials selected from a silane material and a siloxane material.

An embodiment process for hydrogenation of an α,β-substituted moiety of a furan-containing substrate involves reacting the substrate with a composition prepared by combining a copper salt, a phosphine, a polar aprotic solvent, and a material suitable for providing hydrogen for the hydrogenation, under conditions effective for hydrogenation of the α,β-unsaturated moiety.

DETAILED DESCRIPTION

A composition and process for hydrogenation were demonstrated using a substrate derived from non-food based biomass. The substrate was synthesized by reacting methyl furfural with acetone. The substrate is an aldol condensation product, and it is referred to herein as compound A having the structure below.

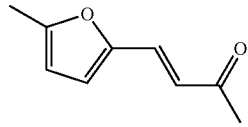

A

Compound A was chosen as a representative substrate for testing the hydrogenation capability of a variety of compositions related to non-food based biomass because compound A includes a furan and a side group that includes both olefin and ketone moieties. The furan, olefin, and ketone are ubiquitous functionalities in biomass-derived materials.

Various combinations of copper compounds, phosphines, and solvents were prepared and tested with compound A on a small scale (NMR tube-scale experiments). The effectiveness of a particular composition was determined after testing the compositions.

Embodiment compositions that were found to be effective for hydrogenation of the α,β-unsaturated group of compound A include the following ingredients: (1) a copper salt; (2) a phosphine ligand; (3) a reductant material that provides hydrogen to the substrate; and (4) a solvent. A preferred solvent is acetonitrile. Other solvents were found to result in hydrogenation, but acetonitrile is preferred. Suitable reductants include silane compounds and siloxane compounds that provide hydrogen for the hydrogenation. An example of a suitable silane compound is phenyl silane. An example of a suitable siloxane compound is polymethylhydrosiloxane. These compositions were found to efficiently hydrogenate both the olefin and ketone of the α,β-unsaturated group and the product formed was a hydrogenated alcohol. The furan group was not affected.

Thirteen commercially available phosphines were tested for hydrogenation of compound A using copper(II) fluoride, benzene-$d_6$ solvent, and phenyl silane. The following phosphines were tested: 1,2-bis(diphenylphosphino)benzene (L1), 1,2-bis(dichlorophosphino)benzene (L2), 1,2-bis(phosphino)benzene (L3), tris(3,5-dimethoxyphenyl)phosphine (L4), tris(4-methoxyphenyl)phosphine (L5), triphenylphosphine (L6), tri-tert-butylphosphine (L7), 1,2-bis(diphenylphosphino)ethane (L8), 1,2-bis(dimethylphosphino)ethane (L9), 1,2-bis(diethylphosphino)ethane (L10), 1,2-bis(dicyclohexylphosphino)ethane (L11), 1,2-bis(pentafluorophenylphosphino)ethane (L12), and 1,3-bis(diisopropylphosphino)propane (L13). A variety of copper salts were tested. Among these is copper (II) fluoride ($CuF_2$), which is believed to react with a silane compound such as phenyl silane or a suitable siloxane (suitable for providing hydrogen) such as polymethylhydrosiloxane to form a copper hydride species which is believed to be a catalyst that reacts with compound A. Phenyl silane ($C_6H_5SiH_3$) is an electrophilic, sterically unencumbered reducing agent. Chemical reactions that included phenyl silane as reductant were worked up with aqueous sodium hydroxide in order to any cleave silyl-ether and silyl enolate hydrosilylation products that were initially formed during the reaction. The hydrogenation of compound A using a composition including copper (II) fluoride, a phosphine, benzene-$d_6$ solvent, and phenyl silane was found to result in compounds B and C, shown below.

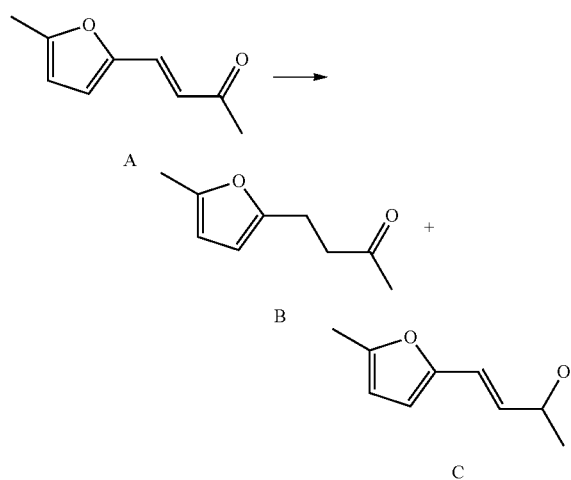

Compound B results from hydrogenation of the olefin, and compound C results from hydrogenation of the ketone. Table 2 below summarizes the percentages of compound B and compound C, the percentage of unreacted compound A, using a composition made by combining copper(II) fluoride, a phosphine, phenyl silane, and benzene-$d_6$ solvent. The hydrogenations were performed under Argon atmosphere. In some cases, the conversion was poor (i.e. much unreacted starting compound A was present). In other cases, conversion was complete and favored olefin hydrogenation (i.e. compound B) compared to ketone hydrogenation (i.e. compound C). In other cases, conversion was complete and favored ketone hydrogenation compared to olefin hydrogenation. In two cases, conversion was complete and the percent of olefin hydrogenation was approximately the same as ketone hydrogenation.

TABLE 1

| Ligand | A | B | C |
| --- | --- | --- | --- |
| L1 | 0 | 100 | 0 |
| L2 | 86 | 14 | 0 |
| L3 | 79 | 15 | 6 |
| L4 | 0 | 100 | 0 |
| L5 | 62 | 14 | 24 |
| L6 | 0 | 83 | 17 |
| L7 | 13 | 81 | 6 |
| L8 | 0 | 21 | 79 |
| L9 | 0 | 7 | 93 |
| L10 | 0 | 0 | 100 |
| L11 | 13 | 73 | 15 |
| L12 | 93 | 7 | 0 |
| L13 | 0 | 52 | 48 |
| L14 | 0 | 48 | 52 |
| None | 0 | 75 | 7 |

As Table 1 shows, ligands L2 and L3 both gave poor conversion (i.e. mostly unreacted compound A). Ligand L4 resulted in complete conversion of compound A to compound B only. Ligand L5 yielded a mixture of 14% compound B and 24% of compound C, but conversion was poor, as 62% of unreacted compound A remained. Poor conversion is likely due to rapid catalyst decomposition. Ligand L6 gave predominantly olefin hydrogenated product compound B, as did tri-tert-butyl phosphine L7. Ligand L8 gave predominantly the ketone reduced compound C (79%). Ligand L9 gave 93% compound C. Ligand L10 gave exclusively compound C. The reactions that employed ligand L9 and ligand L10 were also notable for their speed compared to the reactions employing L1 through L8: while at least several hours were needed for hydrogenation using ligands L1 through L8 (monitored by $^1$H NMR spectroscopy), hydrogenations using ligands L9 and L10 were complete in just the few minutes used to record a $^1$H NMR spectrum. The ligand L11 gave predominantly compound B; the slow hydrogenation using L11 was possible affected by the bulkiness of the cyclohexyl groups. Ligand L12 resulted in hydrogenation to give only 7% of compound B and 93% unreacted compound A. Ligands L13 and L14, both of which have propyl backbones, resulted in approximately a 1:1 mixture of compound B and compound C.

The last entry of Table 2 summarizes results of a hydrogenation having each of the ingredients (i.e. 0.015 millimoles (mmol) CuF$_2$, 400 microliters (μl) of benzene-$d_6$ solvent, 0.1 mmol of compound A, 0.1 millimoles of phenyl silane) of the other hydrogenations involving ligands L1 through L13 with the exception that phosphine was excluded from the composition. The result shown for this last entry demonstrates that even in the absence of a phosphine ligand, hydrogenation of compound A proceeds to completion and results in 75% of compound B and 7% of compound C, and a small amount of compound D in which both the olefin and ketone are hydrogenated. Compound D has the structure below:

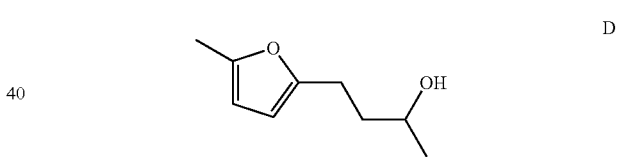

This hydrogenation was slow, taking about 16 hours.

It should be noted that the hydrogenation of the α,β-unsaturated group of a furan-containing compound representative of non-food based biomass, e.g. the hydrogenation of compound A to compound D, in a single pot reaction is an objective of the invention.

For hydrogenations that displayed excellent selectivity and no catalyst decomposition were observed (i.e. using L1 and L10), it is unlikely that hydrogenation catalyzed by unligated copper(II) fluoride affects the observed product ratio. In other reactions, unligated copper(II) fluoride may contribute to some of the observed products; the incomplete conversion observed using L2, L3, L5, and L12 suggests that this might not be the case.

When compound A and phenyl silane were combined without any copper(II) salt or phosphine, no hydrogenation reaction was observed.

It is noted that as the steric bulk of the phosphine increased, olefin reduction appears to be favored. However, increased steric bulk also may prevent the hydrogenation from going to completion. This observation is perhaps best illustrated by L7, which has a Tolman cone angle of 182° and yields predominantly compound B and some compound A.

Ligands L11 and L14, both including cyclohexyl groups, gave significant yields of olefin reduced product, i.e. compound B.

A recent theoretical study indicates that a larger P—Cu—P bite angle may result in a more hydridic Cu—H species (i.e. a presumed catalyst species), which lowers the barrier to ketone reduction; this might explain some of the results shown herein. Ethyl-linked bidentate phosphines generally have larger bite angles than those with benzene linkages, which might explain why L8 gives ketone reduction while L1 does not. The calculated effect of bite angle on the barrier to ketone hydrogenation is small however, and the average bite angle of phosphines with benzene and ethyl linkers differ by only a few degrees. Ligands with propyl backbones have significantly larger bite angles, but those tested here (L13, L14) were not as good for ketone hydrogenation, perhaps due to the steric bulk of isopropyl and cyclohexyl groups of the ligands.

The reaction of compound A with $CuF_2$, L10, and $PhSiH_3$ in $C_6D_6$ proceeded cleanly under an atmosphere of air, giving a 99% yield of compound B and a 1% yield of compound D.

According to prior reports of copper catalyzed hydrogenation, tert-butyl alcohol was often required. By contrast, when tert-butyl alcohol was added to reaction mixtures herein, the effect was only a moderate change in the product distribution. For example, addition of 1 equivalent of tert-butyl alcohol yielded a product distribution of 13% compound B and 87% compound C, while addition of 3 equivalents tert-butyl alcohol gave 21% compound B and 79% compound C.

The most effective ligands for ketone hydrogenation appeared to be L9 and L10. Ligands L9 and L10 are the least sterically bulky of all the ligands tested and are also relatively electron rich. Ligands L9 and L10 have ethylphosphine backbones with Tolman cone angles of 107° and 115°, respectfully, and their alkyl groups are believed to be better donors of electron density to the phosphorus center than phenyl groups, rendering the ligands more electron rich than ligands with phenyl groups, which may promote cleavage of a Cu—H bond and therefore ketone hydrogenation. The observed selectivity for hydrogenation of the ketone moiety in compound A is in contrast to a general preference for Cu—H catalysts to effect 1,4-alkene reduction.

An objective of the invention was a composition and process for hydrogenating both olefin and ketone groups, for example, for converting compound A to compound D, in a one-pot reaction. In view of this objective, experiments were performed using copper(II) fluoride, a phosphine (L10 in particular) and phenyl silane with different solvents. In a hydrogenation, 0.015 mmol of $CuF_2$ and 0.016 mmol of L10 were added to a J. Young valved NMR tube with the appropriate solvent, and then 0.1 mmol of compound A was added, followed by 0.1 mmol of phenyl silane under Argon. The reactions were worked up after about 16 hours with aqueous sodium hydroxide, then extracted 3 times with dichloromethane, and passed through a plug of silica. Table 3 summarizes the results, including yields of compounds A, B, C, and D which were obtained from the $^1$NMR spectra.

TABLE 3

| Solvent | Normalized polarity | Coordination ability | A | B | C | D |
|---|---|---|---|---|---|---|
| $C_6D_6$ | 0.999 | −1.2 | 0 | 0 | 100 | 0 |
| Toluene-$d_8$ | 0.111 | −0.7 | 0 | 7 | 93 | 0 |
| 1,4-dioxane-$d_8$ | 0.164 | −0.4 | 0 | 3 | 88 | 9 |
| $CD_2Cl_2$ | 0.207 | −0.3 | 1 | 28 | 71 | 0 |
| THF-$d_8$ | 0.309 | −1.7 | 0 | 5 | 77 | 18 |
| $CD_3CN$ | 0.444 | 0.3 | 0 | 0 | 16 | 84 |
| DMSO-$d_6$ | 0.460 | −0.2 | 0 | 0 | 28 | 72 |
| $CD_3OD$ | 0.762 | −0.4 | 40 | 33 | 27 | 0 |
| Pyridine/$C_6D_6$ | 0.302 | 1.4 | 0 | 85 | 15 | 0 |

As Table 3 shows, reaction in dioxane-$d_8$ yielded about 9% of compound D. Reaction in THF-$d_8$ yielded about 18% of compound D. The best conversion to compound D was obtained using thoroughly dried polar aprotic solvents. Thus, reaction in DMSO-$d_8$ yielded 72% of compound D, and reaction in $CD_3CN$ yielded 84% of compound D. The presence of water in the solvent resulted in poorer yields, recovery of more compound A (i.e. poorer conversion), and catalyst decomposition.

Thus, the use of dry, polar aprotic solvents gave the desired reactivity, which is rapid reduction of both ketone and olefin moieties in one pot using a single composition. Acetonitrile is a preferred solvent.

The change in reactivity with the solvent does not appear to be due to solvent polarity alone. For example, dichloromethane is a more polar solvent than either THF or dioxane is, yet no compound D was observed when dichloromethane-$d_2$ was used as the solvent.

The observed reactivity also appears to correlate better with the ability of the solvent to coordinate to the metal centers (i.e. their coordination ability, column 3, Table 3). The more positive (or less negative) the coordination ability of a solvent, the better the solvent is as a ligand. According to Table 3, only solvents having a coordination ability greater than −0.4 yielded any compound D. Furthermore, using acetonitrile and DMSO, which have coordination abilities of 0.3 and −0.2 respectively, gave the highest conversion to compound D.

However, a solvent might coordinate too strongly for the hydrogenation to occur. When approximately 2 equivalents of pyridine (the most coordinating of the solvents tested) was added to a reaction in benzene-$d_6$ solvent (the last entry in Table 3), no compound D was obtained. Instead, the major product was the 1,4-reduction product, i.e. compound B.

Having determined that the preferred solvent for conversion of compound A to compound D was acetonitrile, a variety of copper salts were tested in combination with acetonitrile-$d_3$, L10, and phenyl silane for the hydrogenation of compound A. In a typical experiment, 0.015 mmol of copper compound and 0.16 mmol of L10 were added to a J. Young valved NMR tube with $CD_3CN$, and then 0.1 mmol of compound A was added, followed by 0.1 mmol of phenyl silane under Argon. Reactions were worked up after about 16 hours with aqueous sodium hydroxide, then extracted 3 times with dichloromethane, then passed through a silica plug. The yields were determined using $^1H$ NMR spectroscopy. The results are summarized in Table 4.

TABLE 4

| Copper salt | A | B | C | D |
|---|---|---|---|---|
| $CuF_2$ | 0 | 0 | 16 | 84 |
| $Cu(OTf)_2$ | 78 | 22 | 0 | 0 |
| $Cu(BF_4)_2 \cdot 6H_2O$ | 73 | 0 | 7 | 20 |
| $Cu(OAc)_2 \cdot H_2O$ | 0 | 0 | 69 | 31 |
| Cu(OAc) | 0 | 38 | 29 | 33 |
| CuCl | 82 | 18 | 0 | 0 |

TABLE 4-continued

| Copper salt | A | B | C | D |
|---|---|---|---|---|
| CuCl + NaOtBu | 0 | 0 | 13 | 87 |
| CuCl$_2$ | 51 | 49 | 0 | 0 |

In contrast to the generally poor solubility of CuF$_2$, the other copper salts tested were completely soluble upon addition of L10 to the CD$_3$CN. Mostly compound A was observed with the triflate and tetrafluoroborate salts. Both copper(I) (OAc) and the hydrate of Cu(II)(OAc)$_2$ gave similar yields of compound D, wherein compound A was completely consumed, but a significant amount of compound B was observed in the case of Cu(I)(OAc). CuCl gave poor conversion, but addition of sodium tert-butoxide (presumably which reacts with the copper salt to form Copper(I) tert-butoxide) appeared to provide an active catalyst. The products observed using CuF$_2$ or the CuCl/NaOtBu mixture were similar, suggesting the same or similar catalytic species present for these materials. This indicates that the formation of the active catalysts is not affected by the initial oxidation state of the copper center. Despite its poor solubility, CuF$_2$ provided good conversion of compound A to compound D. Copper(II) fluoride is easily stored and handled, making it a preferable copper(II) salt for the hydrogenation reaction.

Reagent grade chemicals and solvents were obtained from ALDRICH, ACROS, or FISHER SCIENTIFIC and used as received. $^1$H and $^{13}$C NMR spectra were recorded on a BRUKER AVANCE 400 MHz spectrometer at ambient temperatures and are referenced to a residual solvent peak. Catalyst screening reactions were prepared in an argon filled glovebox unless otherwise noted. Solvents were pumped into an Argon filled glovebox as received from the manufacturer, opened, and dried over mol. sieves unless otherwise noted. In a typical reaction, 0.015 mmol of CuF$_2$, 0.016 mmol of ligand and 400 microliters of solvent were combined in a J. Young valved NMR tube under Argon in a glovebox. Reactions listed in Table 1 were then heated at 80° C. for 4 hours then cooled to 25° C., while reactions listed in Table 2 and 3 were not heated. Then 0.1 mmol of compound A was added, followed by 0.1 mmol of PhSiH$_3$, while still in the glovebox. Reactions were monitored by $^1$H NMR, and were worked up after 16 hours by stirring with aqueous NaOH for approximately 1 hour, followed by extraction with chloroform or dichloromethane. The resulting organic layer was then passed through a small silica plug. Product yields were determined by integration of $^1$H NMR spectra using a line fitting tool.

In summary, a variety of compositions were tested for hydrogenation of a representative furan-containing molecule derived from non-food based biomass. Bulky aryl phosphine ligands that have been developed for selective reductions were unable to effect reduction of both the olefin and ketone of an α,β-unsaturated ketone moiety in a one-pot reduction. A successful composition was obtained using an electron rich, sterically unencumbered alkyl phosphine and a dry, polar aprotic solvent. Thus, a composition including both bis(diethylphosphino)ethane (L10) and CuF$_2$ in dry acetonitrile gave 84% yield of compound D from compound A in a matter of minutes. The compositions effective for conversion of compound A to compound D are expected to be effective for a one-pot conversion of non-food biomass derived substrates having furan rings with unsaturated moieties including an α,β-unsaturated ketone moieties.

Although the present invention has been described with reference to specific details, it is not intended that such details should be regarded as limitations upon the scope of the invention, except as and to the extent that they are included in the accompanying claims.

What is claimed is:

1. A process for hydrogenation of an α,β-unsaturated ketone moiety of a furan-containing substrate, the process comprising:
    preparing a composition by combining a copper salt, a phosphine, a polar aprotic solvent, and a material suitable for providing hydrogen for the hydrogenation, the suitable material selected from the group consisting of a silane material and a siloxane material; and
    adding the composition to the furan-containing substrate having the α,β-unsaturated keton moiety under conditions effective for hydrogenation of both an olefin moiety and a ketone moiety of the α,β-unsaturated ketone moiety, whereby a furan-containing alcohol is produced.

2. The process of claim 1, wherein the phosphine is selected from the group consisting of bis(diethylphosphino)ethane, 1,3-bis(diisopropylphosphino)propane, and combinations thereof.

3. The process of claim 1, wherein the copper salt includes copper(II) fluoride.

4. The process of claim 1, wherein the copper salt is copper (I) chloride and the composition further includes a material that reacts with copper(I) chloride to provide a composition effective for hydrogenation of both the olefin moiety and the ketone moiety of the α,β-unsaturated ketone moiety of the furan-containing substrate.

5. The process of claim 1, wherein the polar aprotic solvent includes acetonitrile.

6. The process of claim 1, wherein the hydrogen-providing material includes phenyl silane or polymethylhydrosiloxane.

* * * * *